United States Patent
Takasu

(10) Patent No.: US 10,564,086 B2
(45) Date of Patent: Feb. 18, 2020

(54) PARTICLE CONCENTRATION MEASURING APPARATUS WITH HUMIDITY CORRECTION

(71) Applicant: FUJITSU LIMITED, Kawasaki-shi, Kanagawa (JP)

(72) Inventor: Ryozo Takasu, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 482 days.

(21) Appl. No.: 15/137,412

(22) Filed: Apr. 25, 2016

(65) Prior Publication Data

US 2016/0349168 A1 Dec. 1, 2016

(30) Foreign Application Priority Data

May 29, 2015 (JP) ................. 2015-110393

(51) Int. Cl.
*G01N 15/06* (2006.01)
*G01N 5/02* (2006.01)
(Continued)

(52) U.S. Cl.
CPC ............. *G01N 15/06* (2013.01); *G01N 5/02* (2013.01); *G01N 15/1459* (2013.01); (Continued)

(58) Field of Classification Search
CPC ......... F24F 11/0017; G01N 2001/2223; G01N 1/2273; G01N 2001/2276; G01N 1/2208
See application file for complete search history.

(56) References Cited

U.S. PATENT DOCUMENTS 4,570,494 A * 2/1986 Dunn ................... G01N 1/2214 422/88
4,752,131 A * 6/1988 Eisenlauer ............ C02F 1/5209 250/564

(Continued)

FOREIGN PATENT DOCUMENTS

CN 201298012 Y 8/2009
CN 103940713 A 7/2014

(Continued)

OTHER PUBLICATIONS

Machine translation of CN 201298012 Y which originally published on Aug. 26, 2009.*

(Continued)

*Primary Examiner* — David A Rogers
(74) *Attorney, Agent, or Firm* — Kratz, Quintos & Hanson, LLP

(57) ABSTRACT

A measuring apparatus includes a concentration measuring unit that measures a particle number concentration of a particle in gas; a humidity measuring unit that measures humidity of a surrounding to which the particle is exposed when the concentration measuring unit measures the particle number concentration; a first case in which the concentration measuring unit and the humidity measuring unit are accommodated, the first case having a first inlet and a first outlet; and a first exhausting unit that exhausts the gas in the first case from the first outlet; wherein the humidity measuring unit is disposed upstream of the concentration measuring unit in a flow path of the gas from the first inlet to the first outlet.

13 Claims, 17 Drawing Sheets

(51) Int. Cl.
*G01N 15/14* (2006.01)
*G01N 1/22* (2006.01)
*G01N 15/00* (2006.01)

(52) U.S. Cl.
CPC ... *G01N 1/2273* (2013.01); *G01N 2015/0046* (2013.01); *G01N 2015/0693* (2013.01); *G01N 2015/1486* (2013.01)

(56) References Cited

U.S. PATENT DOCUMENTS

| | | | | |
|---|---|---|---|---|
| 4,842,406 A * | 6/1989 | VonBargen | ........ | G01N 15/0205 356/336 |
| 5,254,371 A * | 10/1993 | Hegner | ................ | G01N 27/225 361/178 |
| 5,571,945 A * | 11/1996 | Koutrakis | ......... | G01N 15/0618 73/28.03 |
| 5,572,322 A | 11/1996 | Noda | | |
| 5,619,333 A * | 4/1997 | Staff | .................... | G01N 21/534 356/335 |
| 5,855,849 A * | 1/1999 | Li | ........................ | G01N 27/121 422/88 |
| 5,932,795 A * | 8/1999 | Koutrakis | ............ | G01N 1/2205 422/80 |
| 6,342,295 B1 * | 1/2002 | Kobayashi | ........... | G01N 27/121 338/35 |
| 6,404,494 B1 * | 6/2002 | Masonis | ................ | G01N 21/53 250/574 |
| 6,445,565 B1 * | 9/2002 | Toyoda | ................ | G01N 27/225 257/301 |
| 6,580,600 B2 * | 6/2003 | Toyoda | ................ | G01N 27/225 361/523 |
| 6,615,659 B2 * | 9/2003 | Shibue | ................ | G01N 27/121 324/664 |
| 6,786,105 B1 * | 9/2004 | Sioutas | ................ | G01N 1/2273 73/863.22 |
| 6,815,666 B2 * | 11/2004 | Schroeder | ............... | H01J 49/26 250/281 |
| 6,967,338 B1 * | 11/2005 | Sickenberger | ..... | G01N 15/1459 250/461.1 |
| 7,032,448 B2 * | 4/2006 | Hamamoto | .......... | G01N 27/225 361/280 |
| 7,213,445 B2 * | 5/2007 | Wu | ........................ | G01N 15/06 73/24.03 |
| 7,471,093 B2 * | 12/2008 | Arisaka | ................ | G01N 27/225 324/664 |
| 7,552,635 B2 * | 6/2009 | Chang | .................. | G01N 27/048 73/335.05 |
| 7,947,503 B2 * | 5/2011 | Tuchman | ............. | G01N 1/2205 177/210 FP |
| 8,299,449 B2 * | 10/2012 | Febo | .................. | G01N 15/0625 250/307 |
| 8,351,035 B2 * | 1/2013 | Goohs | .................. | G01N 21/274 356/337 |
| 9,086,341 B2 * | 7/2015 | Tsai | ..................... | G01N 1/2208 |
| 2002/0112550 A1 * | 8/2002 | Lawless | ............... | G01N 1/2273 73/863.21 |
| 2003/0002238 A1 * | 1/2003 | Toyoda | ................ | G01N 27/225 361/302 |
| 2003/0010119 A1 * | 1/2003 | Toyoda | ................ | G01N 27/225 73/335.04 |
| 2005/0076704 A1 * | 4/2005 | Wu | ........................ | G01N 15/06 73/24.03 |
| 2007/0092976 A1 * | 4/2007 | Watson | ................ | G01N 1/2205 436/181 |
| 2009/0081804 A1 * | 3/2009 | Tuchman | ............. | G01N 1/2205 436/158 |
| 2010/0163761 A1 * | 7/2010 | Febo | .................. | G01N 15/0618 250/573 |
| 2010/0218595 A1 * | 9/2010 | Dikken | .............. | B01D 39/1692 73/28.04 |
| 2011/0065097 A1 * | 3/2011 | Jones, Jr. | ................ | A22B 5/007 435/5 |
| 2011/0271739 A1 * | 11/2011 | Goohs | .................... | G01N 15/04 73/28.01 |
| 2011/0277679 A1 * | 11/2011 | Good | .................... | G01N 1/2202 116/202 |
| 2015/0153317 A1 * | 6/2015 | Krebs | ................ | G01N 33/0062 96/397 |
| 2016/0018297 A1 * | 1/2016 | Domaradzki | ........ | G01N 1/2273 73/31.01 |
| 2016/0195462 A1 * | 7/2016 | Zhang | .................. | G01N 15/06 73/31.02 |
| 2017/0246486 A1 * | 8/2017 | Cazier | .................... | A62B 27/00 |
| 2017/0248509 A1 * | 8/2017 | Godoy | .............. | G01N 15/1431 |

FOREIGN PATENT DOCUMENTS

| | | |
|---|---|---|
| CN | 203894139 U | 10/2014 |
| JP | S57-182149 U | 11/1982 |
| JP | H08-15122 | 1/1996 |
| JP | H11-502303 | 2/1999 |

OTHER PUBLICATIONS

Office Action of corresponding Chinese Patent Application No. CN201610343955.6, dated Jul. 4, 2018 (15 Sheets).
Office Action of corresponding Chinese Patent Application No. 201610343955.6 dated Jan. 17, 2019 (5 pages, 10 pages translation, 15 pages total).
Office Action of corresponding Japanese Patent Application No. 2015-110393 dated Feb. 19, 2019 (4 pages, 3 pages translation, 7 pages total).
Office Action of Chinese Patent Application No. 201610343955.6 dated Aug. 5, 2019 (7 sheets, 11 sheets translation, 18 sheets total).

* cited by examiner

FIG. 17

AMBIENT ENVIRONMENT MONITORING SYSTEM  MAY 13, 2015 AT 17:56

AMBIENT ENVIRONMENTAL DATA IN BBBBB TOWN IN AAAAA CITY

LAST 20 MINUTES (FROM 16:28 TO 16:57)

| TIME | TEMPERATURE (°C) | HUMIDITY (%) | ATMOSPHERIC PRESSURE (hPa) | PM2.5 CONCENTRATION (μg/m³) |
|---|---|---|---|---|
| 16:28 | — | — | — | 38.6 |
| 17:26 | 23.1 | 44 | 997.4 | 8.6 |
| 16:40 | 23.5 | 41 | 990.9 | 15.4 |
| 16:41 | 23.5 | 42 | 991.1 | 14.9 |
| 16:42 | 23.5 | 42 | 991.2 | 14.4 |
| 16:43 | 23.5 | 43 | 991.2 | 14.1 |
| 16:44 | 23.5 | 42 | 991.1 | 14.1 |
| 16:45 | 23.5 | 42 | 991.3 | 14.9 |
| 16:46 | 23.5 | 42 | 991.3 | 15.0 |
| 16:47 | 23.5 | 41 | 991.3 | 15.3 |
| 16:48 | 23.5 | 41 | 991.2 | 15.3 |

~78

PARTICLE CONCENTRATION MEASURING APPARATUS WITH HUMIDITY CORRECTION

CROSS-REFERENCE TO RELATED APPLICATION

This application is based upon and claims the benefit of priority of the prior Japanese Patent Application No. 2015-110393, filed on May 29, 2015, the entire contents of which are incorporated herein by reference.

FIELD

The embodiments discussed herein are related to a measuring apparatus and a measuring system, and more particularly to a measuring apparatus that, for example, measures the concentration of particles and a measuring system.

BACKGROUND

Recently, measurements of concentrations of fine particulate matter in the air such as PM2.5 are widely performed. The mass of particles included in gas per unit volume is used as the unit of a concentration of particles in gas. This particle concentration is called a mass concentration. In an example of a standard method of measuring the mass concentration of PM2.5, particles in gas are collected with a filter and their mass is measured (see Japanese National Publication of International Patent Application No. 11-502303, for example). A beta-ray attenuation method is also available as a mass concentration measurement method by which automatic measurement is possible. Concentrations obtained in the filter sampling method and beta-ray attenuation method are mass concentrations. At present, PM2.5 concentrations are generally indicated as mass concentrations. As a simple method, a scattered light detection method is available in which particles in gas are illuminated with light and the number of particles in the gas is measured according to the resulting scattered light.

Japanese Laid-open Patent Publication No. 8-15122 is another example of related art.

SUMMARY

According to an aspect of the invention, a measuring apparatus comprising a concentration measuring unit that measures a particle number concentration of a particle in gas; a humidity measuring unit that measures humidity of a surrounding to which the particle is exposed when the concentration measuring unit measures the particle number concentration, the humidity being used when a mass concentration of the particle in the gas is calculated from information indicating a correlation of a mass of the particle to the humidity of the surrounding to which the particle is exposed, the particle number concentration measured by the concentration measuring unit, and the humidity of the surrounding to which the particle is exposed; a first case in which the concentration measuring unit and the humidity measuring unit are accommodated, the first case having a first inlet and a first outlet; and a first exhausting unit that exhausts the gas in the first case from the first outlet; wherein the humidity measuring unit is disposed upstream of the concentration measuring unit in a flow path of the gas from the first inlet to the first outlet.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 17 illustrates an example of a computer screen.

DESCRIPTION OF EMBODIMENTS

In the method in which a filter is used to collect particles, a time taken in one measurement is, for example, 24 hours or more. Another problem in the method is that automatic measurement is difficult. In the beta-ray attenuation method, automatic measurement is possible, but it is hard to say that the measurement time in the beta-ray attenuation method is sufficiently short. Another problem with the beta-ray attenuation method is that a measuring apparatus is large and expensive. In the scattered light detection method, automatic measurement is possible and a measurement time is short. A measuring apparatus for the scattered light detection method is small and inexpensive. However, a concentration measurable in the scattered light detection method is not a mass concentration but a particle number concentration equivalent to the number of particles in a unit volume. Therefore, precision is lowered when a particle number concentration is converted to a mass concentration.

Accordingly, it is desired to provide a measuring apparatus and measuring system which are able to precisely measure the concentration of particles.

A concentration measurable in a scattered light detection method is not a mass concentration but a particle number concentration equivalent to the number of particles in a unit volume. When a particle number concentration of particles in gas is converted to a mass concentration, the conversion is affected by humidity in the gas. When, for example, humidity in the gas changes, the amount of moisture absorbed by particles also changes, so a distribution of particle diameters and the physical and chemical properties of particles change. Particles are a mixture of various components. The hygroscopic properties of particles vary depending on their components. When a particle is made of, for example, ammonium sulfate, when humidity is 90%, the scattered light cross section of the particle is five times the cross section in a dried state. When a particle is made of an organic substance, its scattered light cross section is not so affected by humidity. As described above, when particles have different components, the particles have different hygroscopic properties. The component of a particle changes with the place and time. Therefore, precision in conversion from a particle number concentration to a mass concentration is lowered. In a measuring system described below, precision in conversion from a particle number concentration to a mass concentration is increased by measuring the hygroscopic properties of particles, so the concentration of particles may be precisely measured.

Figure 1:
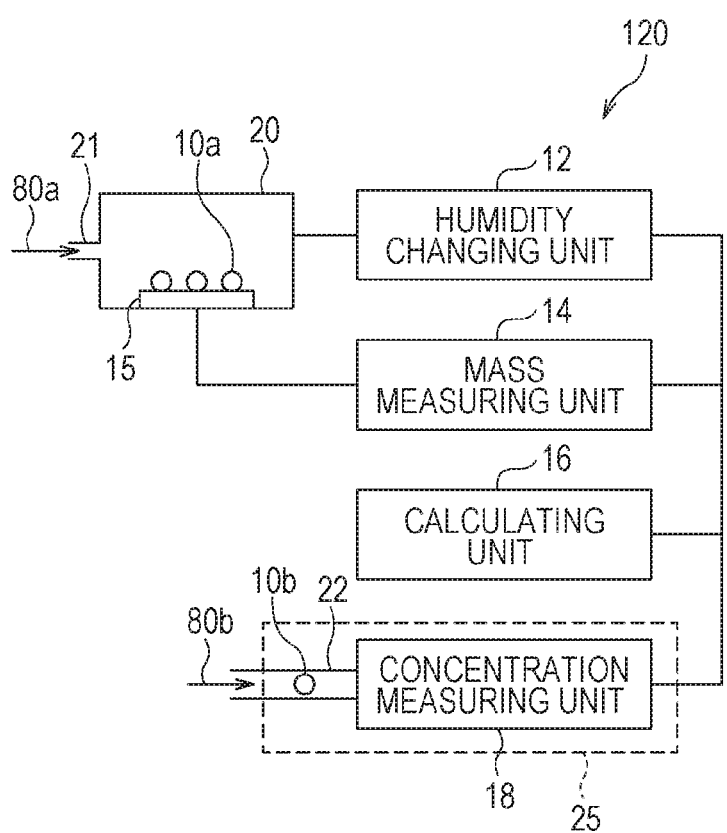
FIG. 1 is a block diagram of a measuring system in which a measuring apparatus in an embodiment is used.
Figure 2:
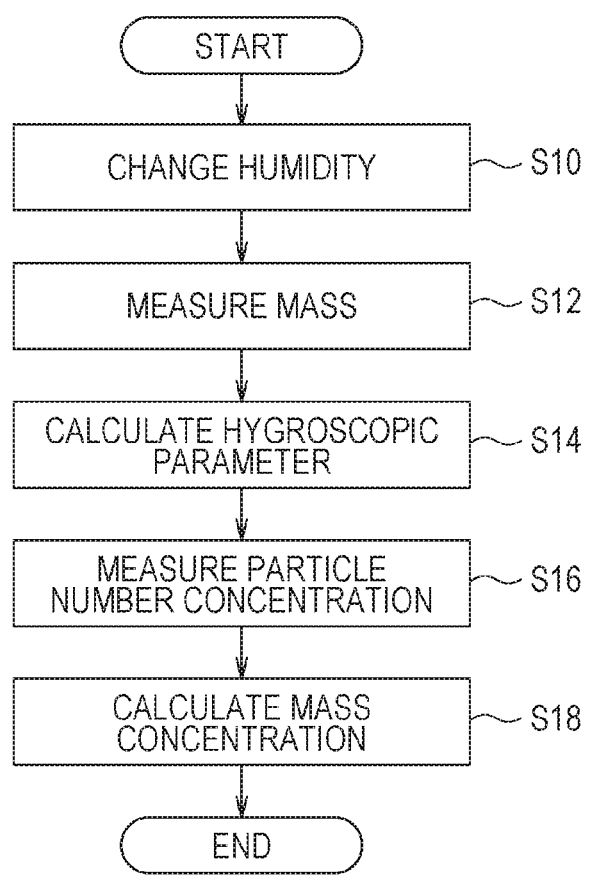
FIG. 2 is a flowchart illustrating a measurement method used by the measuring system in which the measuring apparatus in the embodiment is used.

FIG. 1 is a block diagram of a measuring system in which a measuring apparatus in an embodiment is used. FIG. 2 is a flowchart illustrating a measurement method used by the measuring system in which the measuring apparatus in the embodiment is used.

As illustrated in FIG. 1, a measuring system 120 mainly includes a humidity changing unit 12, a mass measuring unit 14, a calculating unit 16, a measurement chamber 20, and a measuring apparatus 25. The measuring apparatus 25 includes a concentration measuring unit 18 and an inlet 22.

As illustrated in FIG. 1, an inlet 21 leads gas 80a such as the ambient air to the interior of the measurement chamber 20. Particles 10 in the gas 80a adhere to a table 15. The humidity changing unit 12 changes the humidity of a surrounding to which the particles 10 in the measurement chamber 20 are exposed (step S10). The mass measuring unit 14 measures the mass of particles 10a in the gas 80a that have adhered to the table 15 (step S12). The mass measuring unit 14 and table 15 are, for example, a quartz oscillator that, for example, adsorb particles 10a on its surface. The calculating unit 16 calculates a hygroscopic parameter from the relative humidity of the surrounding around the particles 10a and the mass of the particles 10a (step S14). The calculating unit 16 is, for example, a computer or a processor. The hygroscopic parameter is information indicating a correlation of humidity to mass.

After that, gas 80b is guided through the inlet 22 to the concentration measuring unit 18. A particle 10b in the gas 80b has almost the same component as the particle 10a in the gas 80a. For example, the gas 80a and gas 80b are collected in almost the same place at almost the same time. The concentration measuring unit 18 measures the particle number concentration of particles 10b in the gas 80b (step S16). The concentration measuring unit 18 is, for example, a particle number concentration measuring instrument that uses a scattered light detection method. While measuring the particle number concentration of particles 10b, the concentration measuring unit 18 measures the humidity of the gas 80b. The calculating unit 16 calculates the mass concentration of particles 10b in the gas 80b from the particle number concentration and the humidity of the gas 80b measured by the concentration measuring unit 18, and the hygroscopic parameter obtained by the calculating unit 16 (step S18).

Figure 3A:
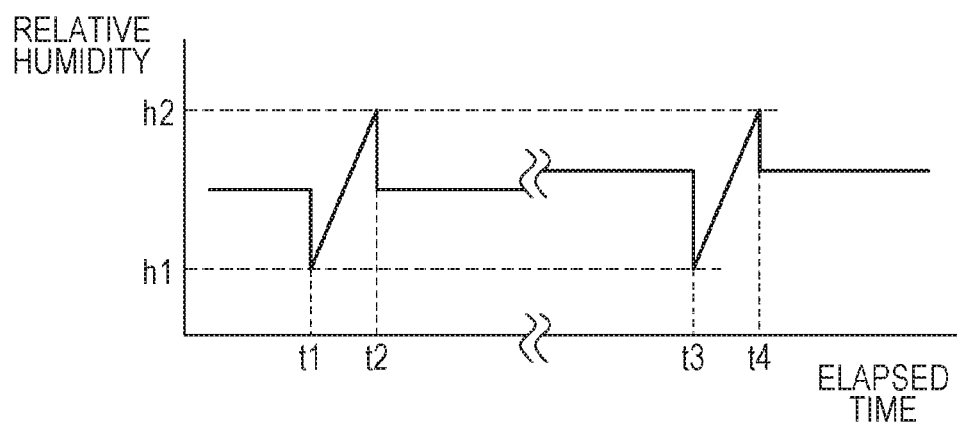
FIG. 3A illustrates changes in relative humidity in a measurement chamber with time.
Figure 3B:
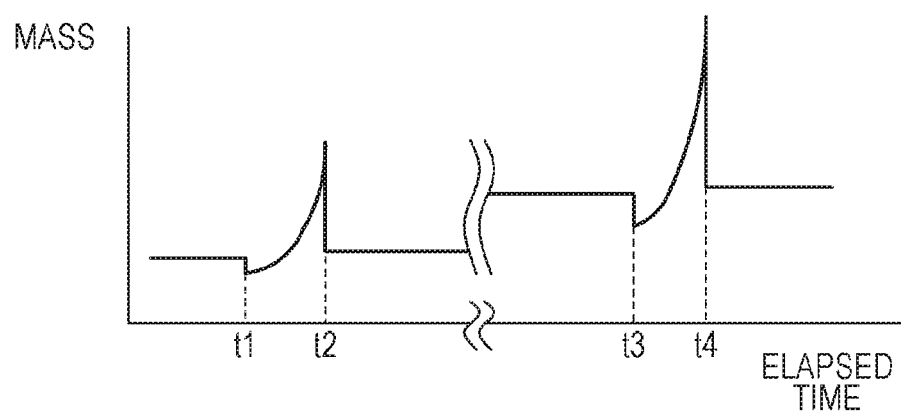
FIG. 3B illustrates changes in mass measured by a mass measuring unit with time.

Now, a method by which the calculating unit 16 calculates the hygroscopic parameter in step S10 to S14 will be described. FIG. 3A illustrates changes in relative humidity in a measurement chamber with time, and FIG. 3B illustrates changes in mass measured by a mass measuring unit with time. During a period to time t2, particles 10a are not collected on the table 15. After time t3, particles 10a are collected on the table 15. Until time t1, the humidity changing unit 12 does not adjust humidity in the measurement chamber 20, so the humidity in the measurement chamber 20 is unpredictable. The mass measured by the mass measuring unit 14 is a certain value. At time t1, the humidity changing unit 12 begins to change the humidity in the measurement chamber 20. The humidity in the measurement chamber 20 at time t1 is h1. The humidity progressively changes during a period from time t1 to time t2. The humidity at time t2 is h2. As the humidity changes, the mass of the table 15 also changes. This is because the surface of the table 15 and/or dust and other substances adhering to the surface absorb moisture.

During a period from time t2 to time t3, particles 10a are collected on the table 15. The humidity is unpredictable immediately before time t3. The mass of the table 15 is increased by an amount by which particles 10a have adhered to the table 15. During a period from time t3 to time t4, the relative humidity in the measurement chamber 20 continuously changes from h1 to h2. As the humidity changes, the mass of the table 15 also changes.

Humidity h1 is, for example, 0%, and humidity h2 is, is for example, 100%. Relative humidity h1 may be humidity (10%, for example) at which adsorption of moisture is negligible. Relative humidity h2 may be the maximum humidity that may be generated in an environment in which the concentration of particles is measured. Relative humidity h1 and relative humidity h2 may be set to arbitrary values in this way.

Figure 4A:
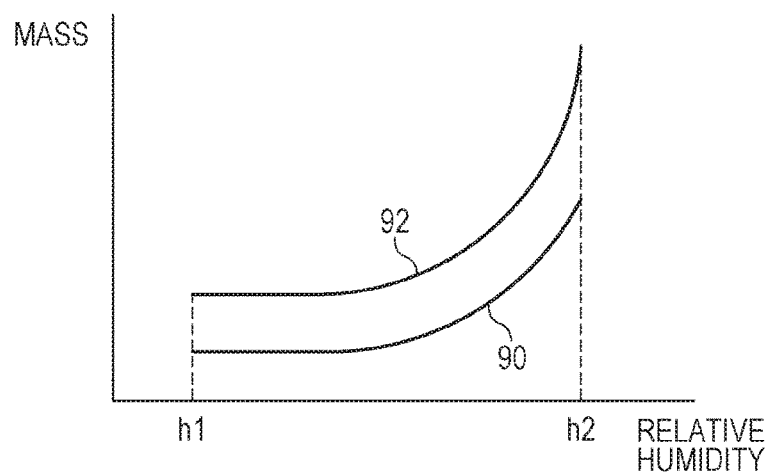
FIGS. 4A to 4C each illustrate a relationship between mass and relative humidity.
Figure 4B:
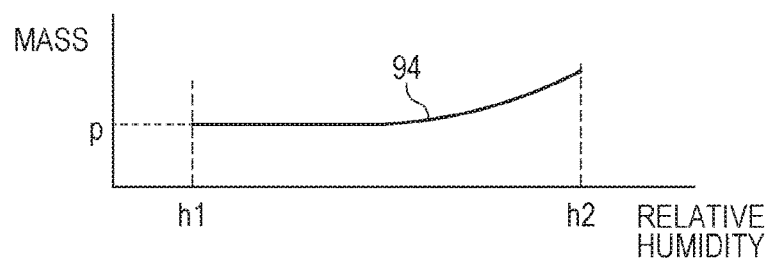
Figure 4C:
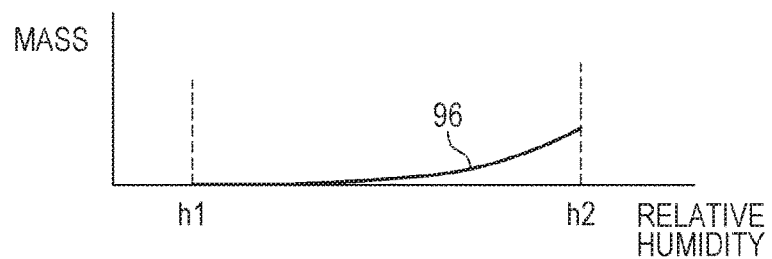

FIGS. 4A to 4C each illustrate a relationship between mass and relative humidity. As illustrated in FIG. 4A, the calculating unit 16 calculates, from FIGS. 3A and 3B, a correlation curve 90 of mass with respect to relative humidity in a period from time t1 to time t2. The calculating unit 16 calculates a correlation curve 92 of mass with respect to relative humidity in a period from time t3 to time t4. As illustrated in FIG. 4B, the calculating unit 16 subtracts the curve 90 from the curve 92 and obtains a curve 94. The curve 94 indicates mass added as a result of particles 10a adhering to the table 15. Mass p at humidity h1 at which almost no moisture is adsorbed to particles 10a is equivalent to the mass of particles 10a that have not adsorbed moisture. As illustrated in FIG. 4C, the calculating unit 16 subtracts mass p from the curve 94 and obtains a curve 96. The curve 96 is equivalent to mass added as a result of particles 10a adsorbing moisture. When the curve 96 is divided by mass p, a hygroscopic parameter a(h) per unit mass is obtained.

The hygroscopic parameter a(h) indicates the mass of moisture that dry particles per unit mass adsorb at relative humidity h.

Next, a method by which the calculating unit 16 calculates a mass concentration in step S18 will be described. The particle number concentration measured by the concentration measuring unit 18 will be denoted Cn, and a mass concentration to be calculated will be denoted Cm. Then, the mass concentration Cm is obtained by the following equation that uses the particle number concentration Cn, humidity h, and the hygroscopic parameter a(h).

$$Cm = k \times Cn \times a(h)$$

where k is a correction coefficient, which is determined from Cm obtained in a method in which a filter is used to collect particles or a beta ray attenuation method, Cn obtained in a scattered light detection method, and a correlation of humidity obtained from an investigation. After k has been determined, Cm is calculated from Cn and a(h).

In the measuring system 120, the calculating unit 16 calculates in advance a hygroscopic parameter for particles 10a the components of which are similar to the components of particles 10b, in the gas 80b, to be measured, as in step S14. The calculating unit 16 then calculates the mass concentration of particles 10b in the gas 80b from the hygroscopic parameter for particles 10a, the particle number concentration of particles 10b in the gas 80b, and the humidity of the gas 80b, as in step S18. The measuring system 120 calculates the mass concentration of particles 10b in this way with the hygroscopic property of particles 10b taken into consideration. The concentration measuring unit 18 measures the particle number concentration of particles 10 in this way. Thus, a measurement time may be shortened. Since the calculating unit 16 calculates the mass concentration of particles 10 from a particle number concentration and humidity, a mass concentration may be precisely calculated.

When the components of particles 10 do not change with time, an interval at which measurement is performed to calculate the hygroscopic parameter may be longer than an interval at which the particle number concentration is measured. The calculated hygroscopic parameter may be stored in a storage unit. When calculating a mass concentration, the calculating unit 16 may obtain the hygroscopic parameter from the storage unit.

When the components of particles 10 do not change depending on the space, the concentration measuring unit 18 may be placed in a plurality of different places in a single place in which measurement is performed to calculate the hygroscopic parameter. As the calculating unit 16, one calculating unit that measures a mass concentration may be provided for each concentration measuring unit 18. Alternatively, one calculating unit that measures a mass concentration may be provided for a plurality of concentration measuring units 18.

First Embodiment

Figure 5:
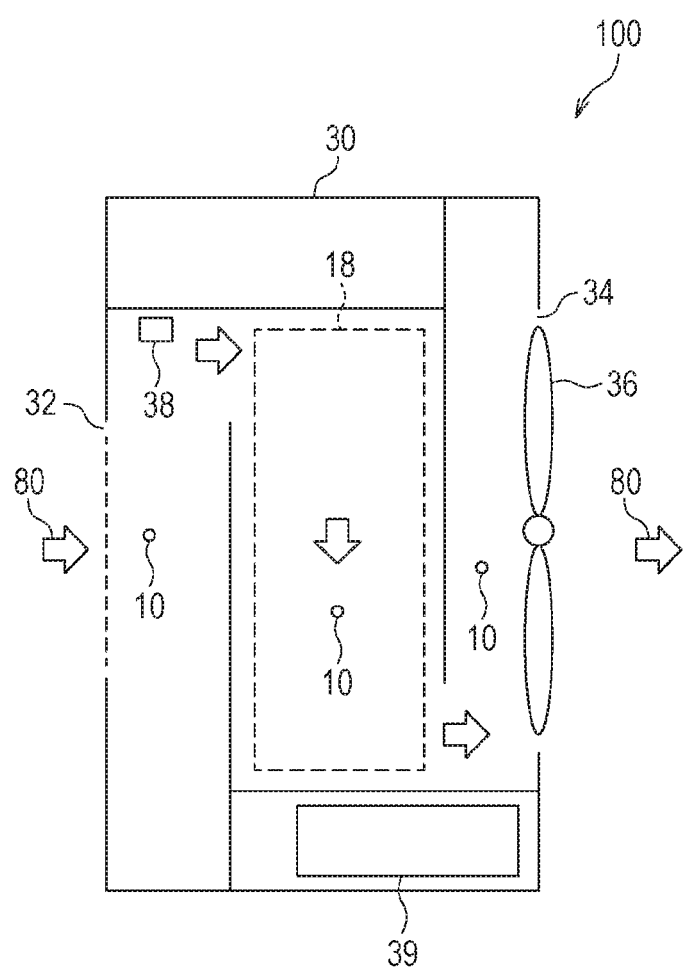
FIG. 5 schematically illustrates a measuring apparatus in a first embodiment.

A first embodiment is an example of the measuring apparatus 25, which is used in, for example, the measuring system 120 in FIG. 1. FIG. 5 schematically illustrates a measuring apparatus in the first embodiment. As illustrated in FIG. 5, a measuring apparatus 100 includes a case 30, a concentration measuring unit 18, an exhaust fan 36 (first exhausting unit), a humidity sensor 38 (humidity measuring unit), and a power supply unit 39. The concentration measuring unit 18 measures the particle number concentration of particles 10 in gas. The humidity sensor 38 measures the humidity of a surrounding to which the particles 10 are exposed. The case 30 accommodates the concentration measuring unit 18, humidity sensor 38, and power supply unit 39. The case 30 includes an inlet 32 (first inlet) through which gas is inhaled into the case 30 (first case), and also includes an outlet 34 (first outlet) from which the gas in the case 30 is exhausted. The exhaust fan 36 exhausts the gas in the case 30 from the outlet 34. The power supply unit 39 supplies electric power to the concentration measuring unit 18, humidity sensor 38, and exhaust fan 36. Gas flows as indicated by arrows 80. A gas flow path from the inlet 32 to the outlet 34 is along the arrows 80.

In the first embodiment, the case 30 accommodates the concentration measuring unit 18 and humidity sensor 38. Thus, the concentration measuring unit 18 and humidity sensor 38 may be appropriately protected. In the gas flow path from the inlet 32 to the outlet 34, the humidity sensor 38 is disposed upstream of the concentration measuring unit 18. Accordingly, when the concentration measuring unit 18 measures the particle number concentration of particles 10, humidity around particles 10 may be more precisely measured with the humidity sensor 38. When the humidity sensor 38 is disposed, for example, downstream of the concentration measuring unit 18, the temperature of the gas may be raided due to heat generated by the concentration measuring unit 18 and the humidity measured by the humidity sensor 38 may be inaccurate.

Second Embodiment

Figure 6:
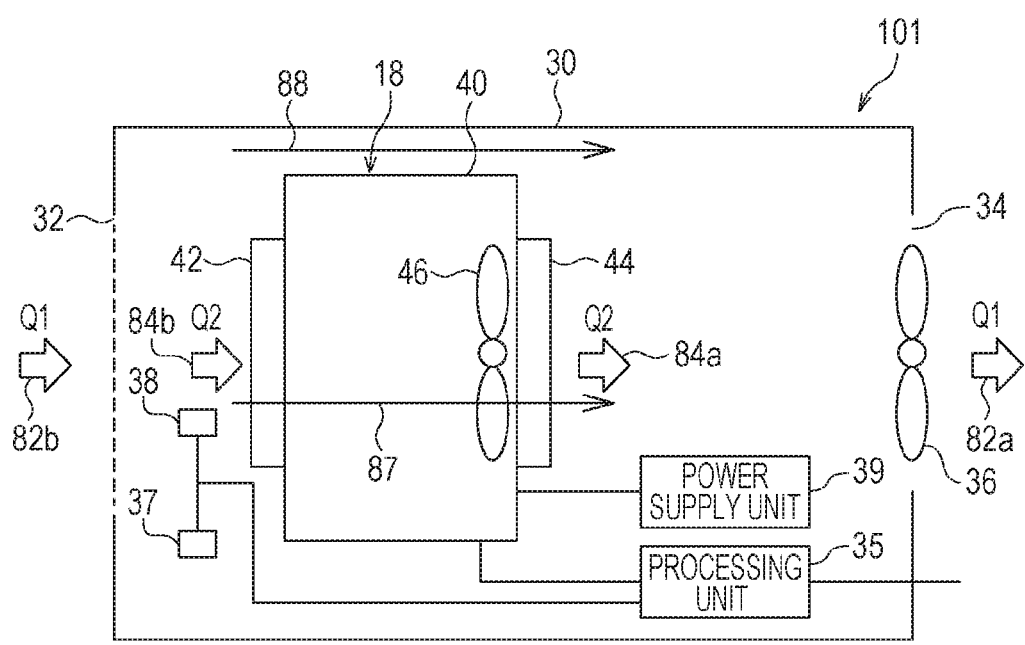
FIG. 6 schematically illustrates a measuring apparatus in a second embodiment.

A second embodiment is an example in which the concentration measuring unit 18 having a case is accommodated in the case 30. FIG. 6 schematically illustrates a measuring apparatus in the second embodiment. As illustrated in FIG. 6, the concentration measuring unit 18 has a case 40 (second case). The case 40 has an inlet 42 (second inlet) through which gas is inhaled into the case 40, and also has an outlet 44 (second outlet) from which the gas in the case 40 is exhausted to the interior of the case 30. The concentration measuring unit 18 has an exhaust fan 46 (second exhausting unit) that exhausts the gas in the case 40 to the interior of the case 30. The exhaust fan 36 exhausts the gas in the case 30 at a flow rate Q1 as indicated by an arrow 82a. Thus, gas is inhaled from the inlet 32 into the case 30 as indicated an arrow 82b at the flow rate Q1. The exhaust fan 46 exhausts the gas in the case 40 at a flow rate Q2 as indicated by an arrow 84a. Thus, gas is inhaled from the inlet 42 into the case 40 at the flow rate Q2 as indicated by an arrow 84b.

The humidity sensor 38, an atmospheric pressure sensor 37 (atmospheric pressure measuring unit), the power supply unit 39, and a processing unit 35 are accommodated in the case 30. The atmospheric pressure sensor 37 measures atmospheric pressure in a surrounding around particles 10. The measured atmospheric pressure is used to correct the particle number concentration measured by the concentration measuring unit 18. The particle number concentration is the number of particles 10 per unit volume at a standard atmospheric pressure (one atmosphere, for example). When the atmospheric pressure around particles 10 differs from the standard atmospheric pressure, correction is preferably performed. The atmospheric pressure sensor 37 may not be provided. The processing unit 35 is, for example, a processor. The processing unit 35 sends information about the humidity measured by the humidity sensor 38, information about the atmospheric pressure measured by the atmospheric pressure sensor 37, and information about the particle number concentration measured by the concentration measuring unit 18 to an external device. Alternatively, the processing unit 35 may calculate a mass concentration from the information about the humidity, the information about the atmospheric pressure, and the information about the particle number concentration, and may send information about the mass concentration to an external device. In other respects, the structure is the same as in the first embodiment; their description will be omitted.

Figure 7:
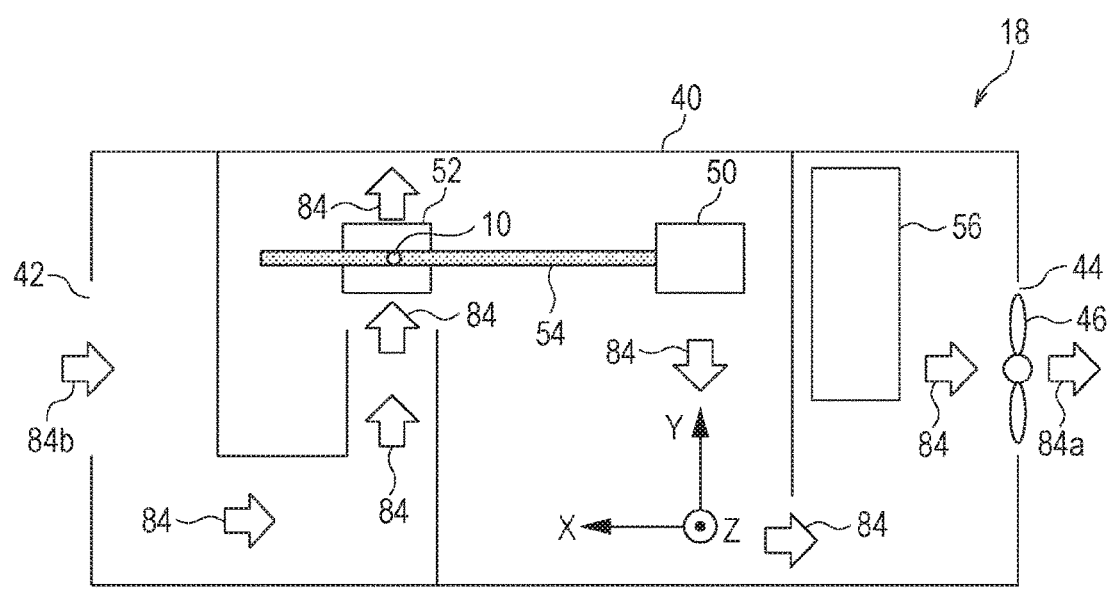
FIG. 7 schematically illustrates a concentration measuring unit used in the second embodiment.

FIG. 7 schematically illustrates the concentration measuring unit used in the second embodiment. The concentration measuring unit 18 has a light source 50 (a laser, for example), a scattered light detector 52 (a photodiode, for example), and a circuit unit 56 in the case 40. A gas flow path in the case 40 is as indicated by arrows 84. The light source 50 emits light 54 (laser beams, for example) to gas inhaled from the inlet 42. For example, a direction in which the light 54 is emitted, the direction of the gas flow path, and a direction in detection by the scattered light detector 52 are mutually orthogonal. The direction in which the light 54 is emitted will be referred to as the X direction, and the direction of the gas flow path will be referred to as the Y direction. The scattered light detector 52 is disposed in the −Z direction of the light 54, and a field of view (detection direction) in detection by the scattered light detector 52 is in the +Z direction. When particles 10 pass through the field of view of the scattered light detector 52 while being carried by gas flow, pulse-like scattered light is generated. The scattered light detector 52 detects the pulse-like scattered light and outputs pulse signals accordingly. The number of pulse signals is the number of particles 10. The concentration of particles 10 is the number of particles 10 included in gas per unit volume. When the flow rate is assumed to be unchanged, a certain volume corresponds to a certain time. Therefore, the number of particles 10 (number of pulse signals) in a certain time is counted. As a result, the particle number concentration of particles 10 may be measured. As described above, the atmospheric pressure measured by the atmospheric pressure sensor 37 may be used to correct the particle number concentration. The circuit unit 56 is a power supply circuit that supplies electric power to the light source 50, the scattered light detector 52, and a processing circuit that counts the number of pulses.

In the second embodiment, the concentration measuring unit 18 includes the case 40 and the exhaust fan 46 that exhausts the gas in the case 40 from the outlet 44. In this structure as well, the humidity sensor 38 is disposed upstream of the concentration measuring unit 18 in the gas flow path from the inlet 32 to the outlet 34. Accordingly, when the concentration measuring unit 18 measures the particle number concentration of particles 10, humidity around particles 10 may be more precisely measured with the humidity sensor 38.

Figure 8A:
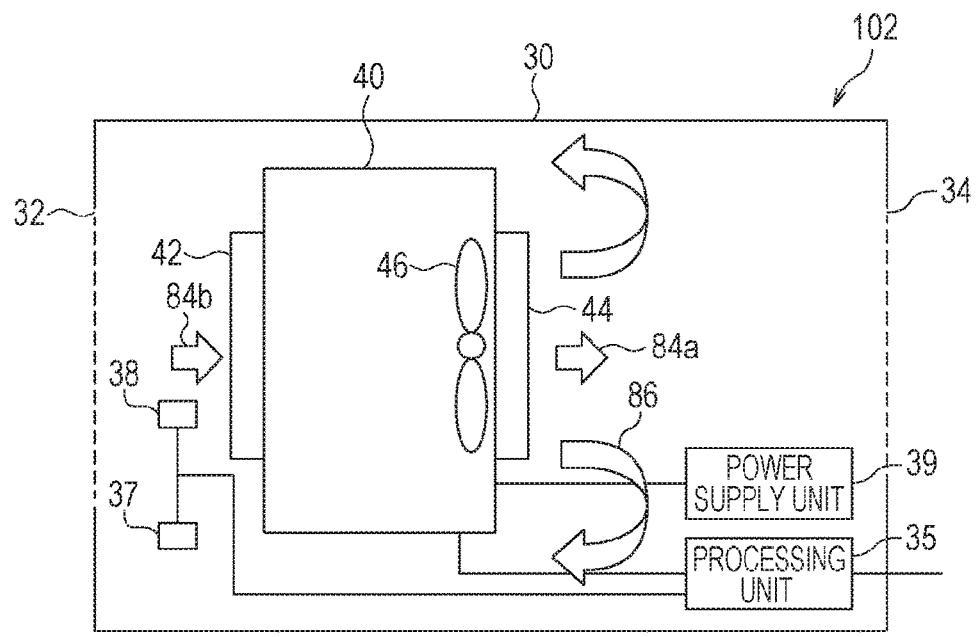
FIG. 8A schematically illustrates a measuring apparatus in a first modification of the second embodiment, and FIG. 8B schematically illustrates a measuring apparatus in a second modification of the second embodiment.
Figure 8B:
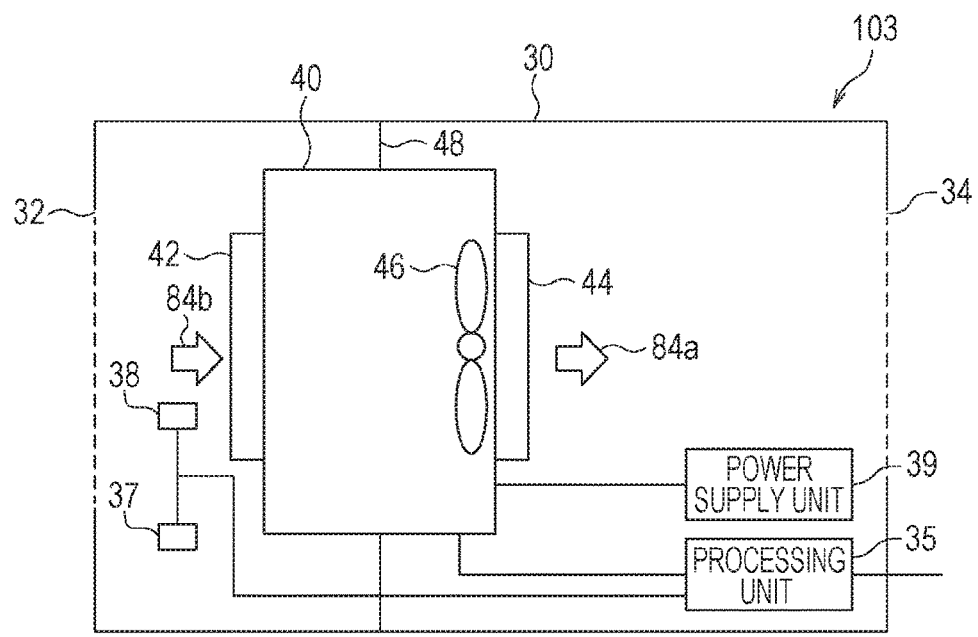

FIG. 8A schematically illustrates a measuring apparatus in a first modification of the second embodiment, and FIG. 8B schematically illustrates a measuring apparatus in a second modification of the second embodiment. As illustrated in FIG. 8A, a measuring apparatus 102 in the first modification of the second embodiment lacks the exhaust fan 36. In other respects, the structure is the same as in the second embodiment; their description will be omitted.

In the first modification of the second embodiment, gas is inhaled into the case 30 and is exhausted from the case 30 by natural diffusion. Therefore, an environment in the case 30 and an environment outside it differ (for example, the concentration of particles 10, humidity, temperature, and the like differ between the inside and outside of the case 30). This reduces precision in concentration measurement and slows a response of concentration measurement. In addition, heat generated from the concentration measuring unit 18, a power supply unit 29, the processing unit 35, and the like are not easily exhausted, so the environment in the case 30 (such as humidity and temperature) differs from the external environment. Furthermore, particles 10 adhere to, for example, the inner surfaces of the case 40 that are located in the flow path in the case 40. These particles 10 are released from the case 40. Therefore, the concentration of particles 10 in the gas exhausted from the case 40 differs from the concentration of particles 10 included in the gas inhaled into the case 40. When the gas exhausted by the concentration measuring unit 18 turns around to the inlet 42 of the case 40 as indicated by arrows 86, measured values of the particle number concentration may become inaccurate.

A possible solution to the problem with first modification of the second embodiment described above is the second modification of the second embodiment. As illustrated in FIG. 8B, in a measuring apparatus 103 in the second modification of the second embodiment, the inlet 42 and outlet 44 of the case 40 are separated from each other by partition walls 48. In other respects, the structure is the same as in the first embodiment; their description will be omitted.

In the measuring apparatus 103 in the second modification of the second embodiment, gas enters the case 30 due to gas flow caused by the exhaust fan 46. Heat generated from the concentration measuring unit 18, power supply unit 29, processing unit 35, and the like is easily exhausted. Thus, the environment in the case 30 may be approximated to the environment outside the case 30. It is also possible to suppress the gas exhausted from the case 40 from turning around to the inlet 42.

The power supply unit 39, which supplies electric power to the concentration measuring unit 18, is preferably disposed downstream of the concentration measuring unit 18 in the gas flow path from the inlet 32 to the outlet 34. Then, it is possible to suppress heat generated in the power supply unit 39 from affecting the humidity sensor 38 and concentration measuring unit 18. The processing unit 35 is preferably disposed downstream of the concentration measuring unit 18. Then, it is possible to suppress heat generated in the processing unit 35 from affecting the humidity sensor 38 and concentration measuring unit 18.

However, a total fluid resistance of the measuring apparatus 103 when viewed from the exhaust fan 46 is larger than in a case in which the concentration measuring unit 18 is used alone. Accordingly, the flow rate of the gas passing the interior of the concentration measuring unit 18 is lower than in a case in which the concentration measuring unit 18 is used alone. When a volume is estimated in terms of time, when the flow rate is different, the particle number concentration may become inaccurate.

In the second embodiment, there are two gas flow paths from the inlet 32 to the outlet 34 as illustrated in FIG. 6; one is a flow path 87 that passes the interior of the case 40 and the other is a path 88 that passes between the case 30 and the case 40 without passing the interior of the case 40. This may suppress the flow rate of the gas passing the interior of the concentration measuring unit 18 from differing from a case in which the concentration measuring unit 18 is used alone. The flow rate Q1 caused by the exhaust fan 36 is larger than the flow rate Q2 caused by the exhaust fan 46. This may suppress the gas exhausted by the exhaust fan 46 from turning around to the inlet 42, unlike the air flows illustrated in FIG. 8A. Then, it is possible to suppress gas having humidity, temperature and/or a concentration of particles 10 different from the outside of the case 30 from turning around to the inlet 42, so the particle number concentration may be precisely measured.

Preferably, the gas to be inhaled by the concentration measuring unit 18 quickly follows changes in the external gas (such as a change in humidity and/or the concentration of particles 10). In view of this, when n designates an interval of measurements by the concentration measuring unit 18 and V designates the volume of a space, in the gas flow path, between the case 30 and the case 40 from the inlet 42 to the inlet 32, then the flow rate Q1 caused by the exhaust fan 46 is V/n or more. Thus, the gas in the volume V may be replaced with an external gas at least once within the interval of measurements by the concentration measuring unit 18.

Figure 9A:
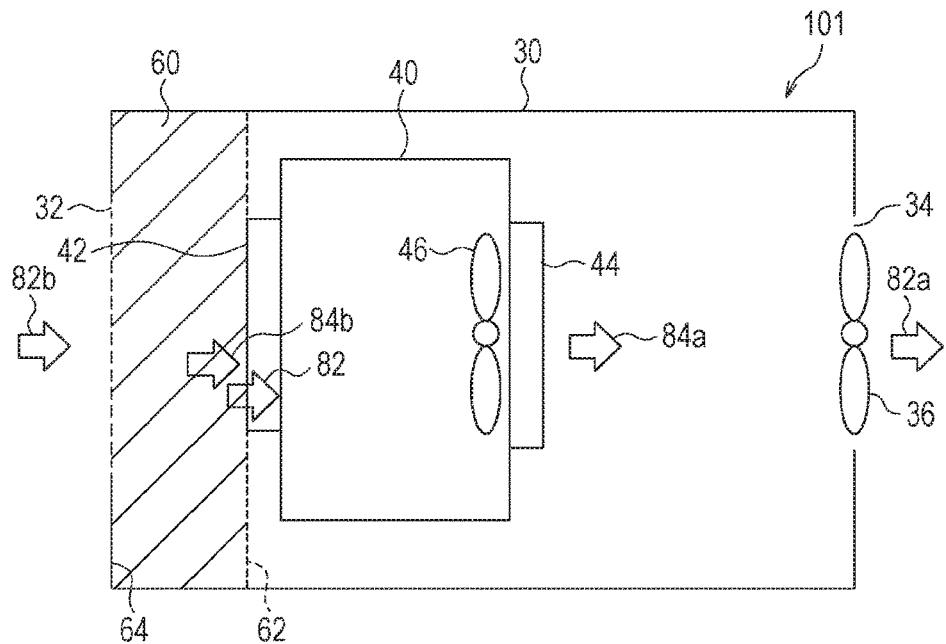
FIG. 9A schematically illustrates the measuring apparatus in the second embodiment, and FIG. 9B schematically illustrates a measuring apparatus in a third modification of the second embodiment.
Figure 9B:
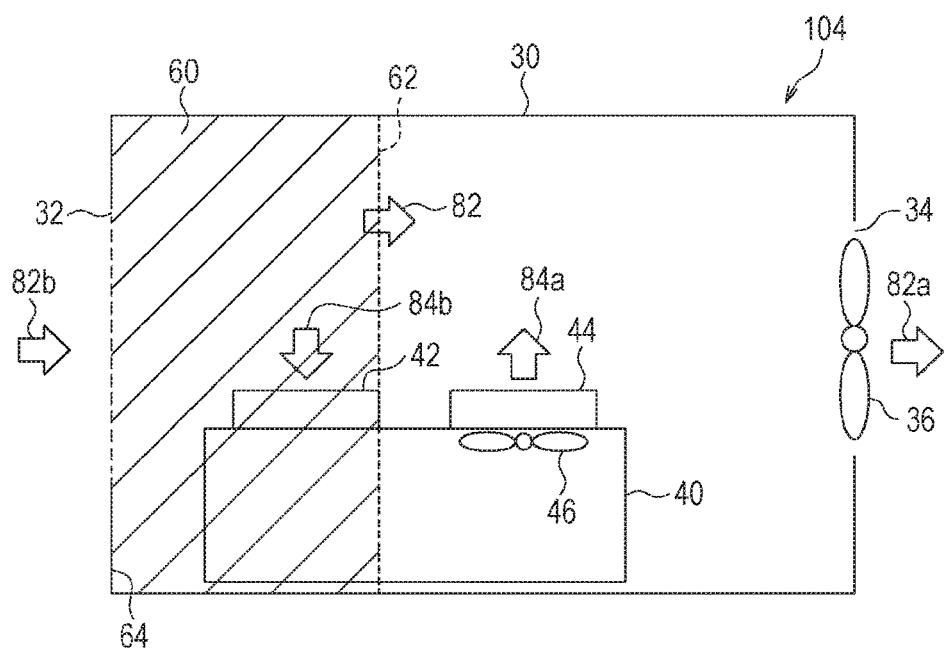
Figure 10A:
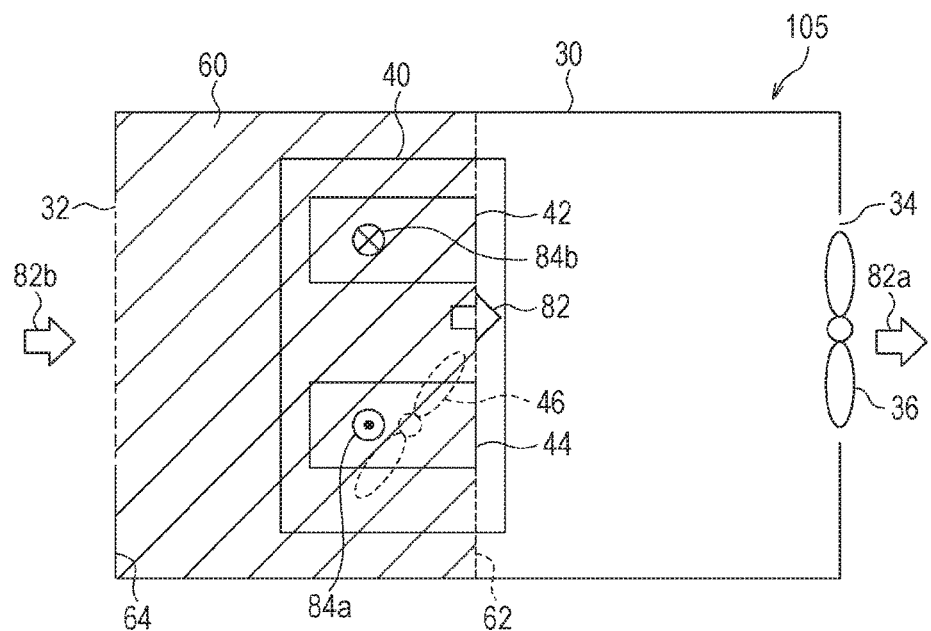
FIG. 10A schematically illustrates a measuring apparatus in a fourth modification of the second embodiment, and FIG. 10B schematically illustrates a measuring apparatus in a fifth modification of the second embodiment.
Figure 10B:
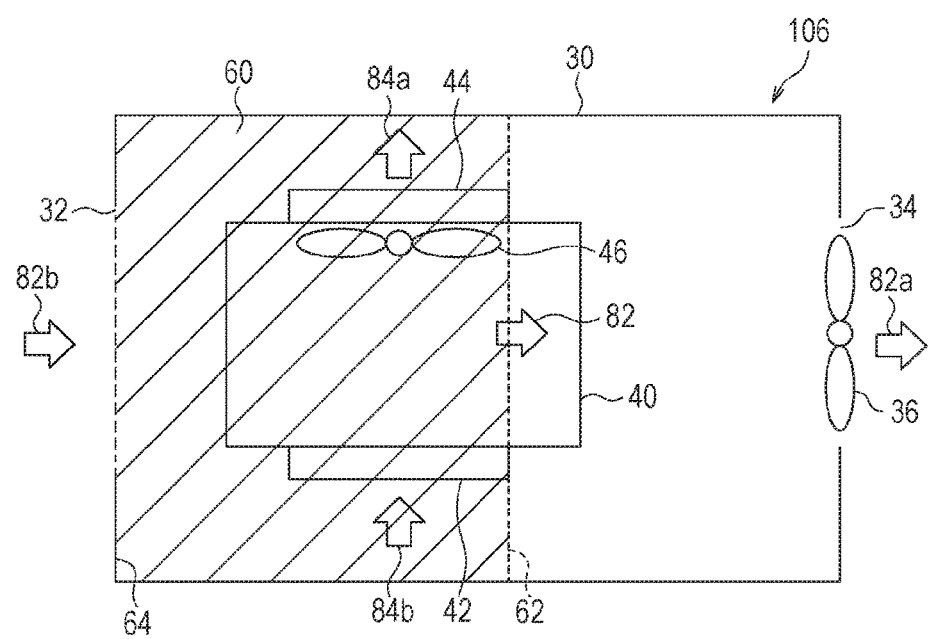

A method of obtaining the volume V will be described below. FIG. 9A schematically illustrates the measuring apparatus in the second embodiment, FIG. 9B schematically illustrate a measuring apparatus in a third modification of the second embodiment, FIG. 10A schematically illustrates a measuring apparatus in a fourth modification of the second embodiment, and FIG. 10B schematically illustrates a measuring apparatus in a fifth modification of the second embodiment. The humidity sensor 38, atmospheric pressure sensor 37, power supply unit 39, and processing unit 35 are not illustrated in FIGS. 9A to 10B.

In the measuring apparatus 101 in the second embodiment, the gas flow direction, indicated by the arrow 84b, near the inlet 42 is almost parallel to the gas flow direction, indicated by an arrow 82, in the case 30, and is also almost parallel to the gas flow direction, indicated by the arrow 84a, near the outlet 44. In this case, the volume V is the volume of a space 60 enclosed by a plane 62 including the inlet 42 and an internal surface 64 of the case 30, the internal surface 64 including the inlet 32, as illustrated in FIG. 9A.

In a measuring apparatus 104 in the third modification of the second embodiment, the gas flow direction, indicated by the arrow 84b, near the inlet 42 is orthogonal to the gas flow direction, indicated by the arrow 82, in the case 30, as illustrated in FIG. 9B. The gas flow direction, indicated by the arrow 84b, near the inlet 42 is opposite to the gas flow direction, indicated by the arrow 84a, near the outlet 44. The inlet 42 is disposed closer to the inlet 32 than to the outlet 44. In this case, the volume V is the volume of the space 60 enclosed by the case 40, the internal surface 64 including the inlet 32, and the plane 62, which is orthogonal to the gas flow direction, indicated by the arrow 82, in the case 30 and includes the end of the inlet 42 in the downstream direction of the gas flow in the case 30.

In a measuring apparatus 105 in the fourth modification of the second embodiment, the gas flow direction, indicated by the arrow 84b, near the inlet 42 is orthogonal to the gas flow direction, indicated by the arrow 82, in the case 30, as illustrated in FIG. 10A. The gas flow direction, indicated by the arrow 84b, near the inlet 42 is opposite to the gas flow direction, indicated by the arrow 84a, near the outlet 44. The inlet 42 and outlet 44 are located at the same distance from the inlet 32. In this case, the volume V is the volume of the space 60 enclosed by the case 40, the internal surface 64 including the inlet 32, and the plane 62, which is orthogonal to the gas flow direction, indicated by the arrow 82, in the case 30 and includes the end of the inlet 42 in the downstream direction of the gas flow in the case 30.

In a measuring apparatus 106 in the fifth modification of the second embodiment, the gas flow direction, indicated by the arrow 84b, near the inlet 42 is orthogonal to the gas flow direction, indicated by the arrow 82, in the case 30, as illustrated in FIG. 10B. The gas flow direction, indicated by the arrow 84b, near the inlet 42 is the same as the gas flow direction, indicated by the arrow 84a, near the outlet 44. In this case, the volume V is the volume of the space 60 enclosed by the case 40, the internal surface 64 including the inlet 32, and the plane 62, which is orthogonal to the gas flow direction, indicated by the arrow 82, in the case 30 and includes the end of the inlet 42 in the downstream direction of the gas flow in the case 30.

In the second embodiment and its third to fifth modifications, as illustrated in FIGS. 9A to 10B, the volume V is the volume of the space 60 enclosed by the plane 62, the internal surface 64 including the inlet 32, and the case 40. The plane 62 is orthogonal to the gas flow direction, indicated by the arrow 82, in the case 30 and includes the end of the inlet 42 in the downstream direction of the gas flow in the case 30.

Figure 11A:
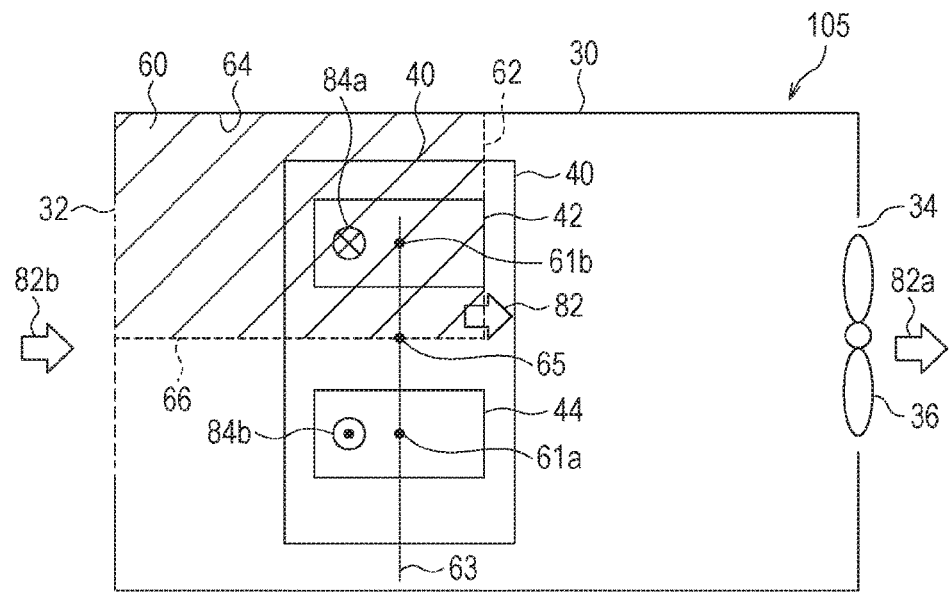
FIG. 11A schematically illustrates the measuring apparatus in the fourth modification of the second embodiment, and FIG. 11B schematically illustrates the measuring apparatus in the fifth modification of the second embodiment.
Figure 11B:
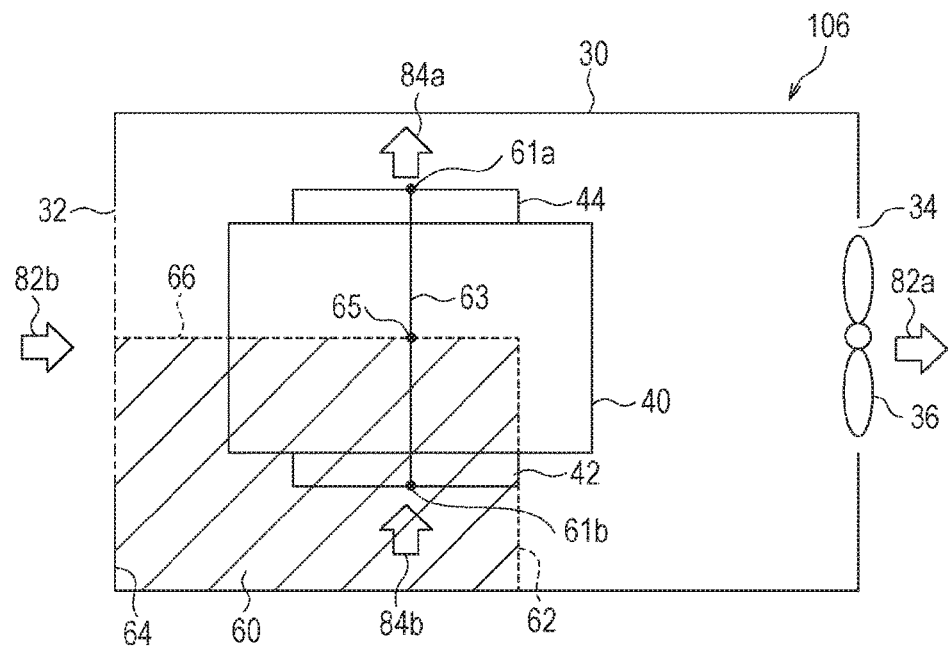

Next, a preferable space in which the humidity sensor 38 is disposed will be described. FIG. 11A schematically illustrates the measuring apparatus in the fourth modification of the second embodiment, and FIG. 11B schematically illustrates the measuring apparatus in the fifth modification of the second embodiment. The humidity sensor 38, atmospheric pressure sensor 37, power supply unit 39, and processing unit 35 are not illustrated in FIGS. 11A and 11B.

In the measuring apparatus 101 in the second embodiment, the humidity sensor 38 is disposed in the space 60 enclosed by the plane 62 including the inlet 42 and the internal surface 64 of the case 30, the internal surface 64 including the inlet 32, as illustrated in FIG. 9A. In the measuring apparatus 104 in the third modification of the second embodiment, the humidity sensor 38 is disposed in the space 60 enclosed by the plane 62, the internal surface 64 including the inlet 32, and the case 40 as illustrated in FIG. 9B. Thus, the humidity sensor 38 may be disposed upstream of the concentration measuring unit 18, which is a heat source.

In the second embodiment and its third modification, the direction in which the inlet 42 and outlet 44 are placed is the same as the gas flow direction, indicated by the arrow 82, in the case 30, as illustrated in FIGS. 9A and 9B. In this state, the humidity sensor 38 is disposed in the space 60 enclosed by the plane 62, the internal surface 64 including the inlet 32, and the case 40. Thus, the humidity sensor 38 may be disposed upstream of the inlet 42. The atmospheric pressure sensor 37 is preferably disposed in the space 60. The direction in which the inlet 42 and outlet 44 are placed is a direction from the center of the inlet 42 toward the center of the outlet 44.

In the measuring apparatus 105 and measuring apparatus 106 respectively in the fourth and fifth modifications of the second embodiment, the inlet 42 and outlet 44 are at the same distance from the inlet 32, as illustrated in FIGS. 11A and 11B. In this case, it is preferable for the gas exhausted from the outlet 44 not to affect the humidity sensor 38. A straight line connecting the center 61b of the inlet 42 and the center 61a of the outlet 44 will be referred to as a straight line 63, and the midpoint between the center 61a and the center 61b will be referred to as the midpoint 65. The humidity sensor 38 is disposed in the space 60 enclosed by a plane 66, which passes the midpoint 65 and is orthogonal to the straight line 63, the plane 62, the internal surface 64, and the case 40. Thus, the humidity sensor 38 may be disposed upstream of the concentration measuring unit 18, which is a heat source.

In the fourth and fifth modifications of the second embodiment, the inlet 42 and outlet 44 are placed in a direction different from the gas flow direction, indicated by the arrow 82, in the case 30, as illustrated in FIGS. 11A and 11B. In this state, the humidity sensor 38 is disposed in the space 60 enclosed by the plane 62, internal surface 64, plane 66, and the case 40. Thus, the humidity sensor 38 may be disposed upstream of the inlet 42. The atmospheric pressure sensor 37 is preferably disposed in the space 60.

Figure 12A:
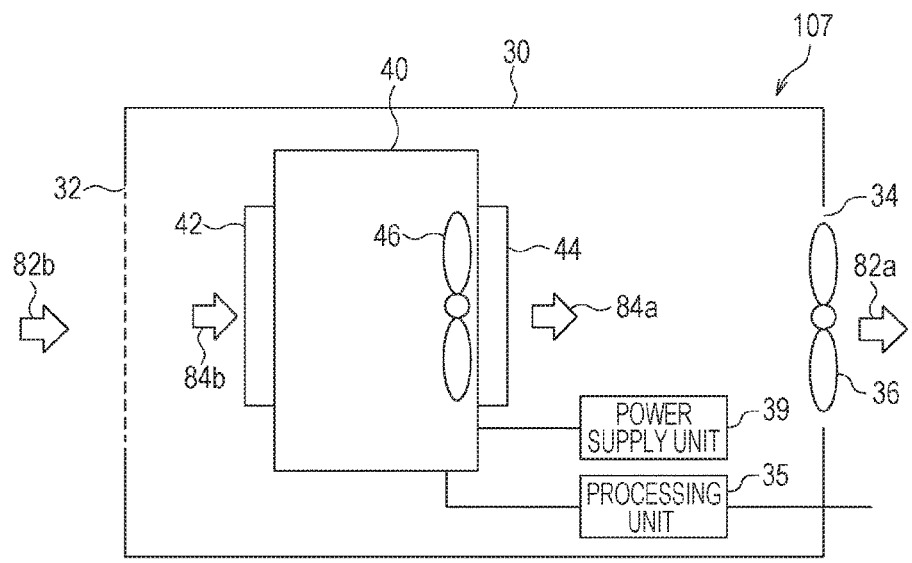
FIG. 12A schematically illustrates a measuring apparatus in a sixth modification of the second embodiment, and FIG. 12B schematically illustrates the case of the concentration measuring unit.
Figure 12B:
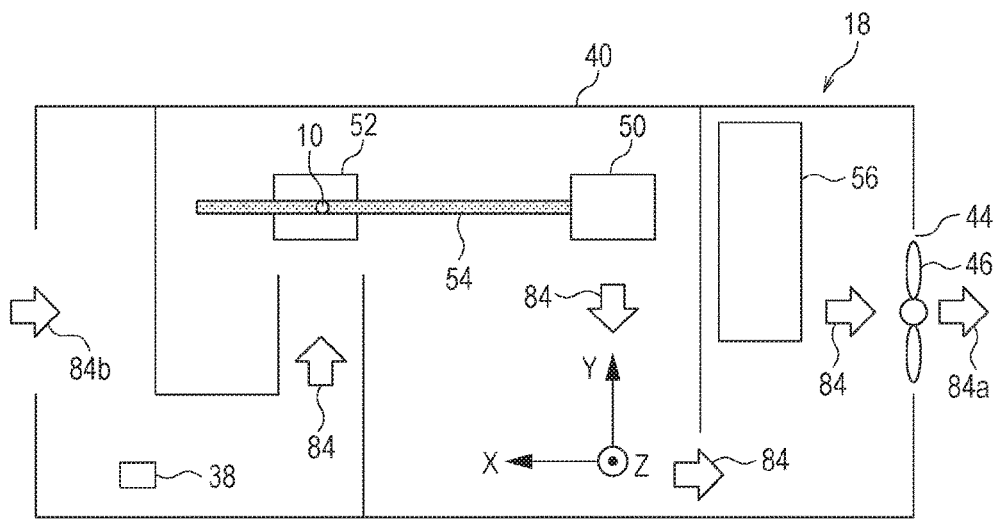

FIG. 12A schematically illustrates a measuring apparatus in a sixth modification of the second embodiment, and FIG. 12B schematically illustrates the case of the concentration measuring unit. In a measuring apparatus 107, the humidity sensor 38 is not disposed outside the case 40, as illustrated in FIG. 12A. In the case 40, the humidity sensor 38 is disposed upstream of the light source 50 and scattered light detector 52, as illustrated in FIG. 12B. In other respects, the structure is the same as in the second embodiment.

As in the sixth modification of the second embodiment, the humidity sensor 38 may be disposed in the case 40. In this case, when the light source 50 and scattered light detector 52 are used as the concentration measuring unit, the humidity sensor 38 is disposed upstream of the concentration measuring unit. The light source 50 may generate much more heat than the scattered light detector 52. Therefore, the humidity sensor 38 is preferably disposed upstream of at least the light source 50. Furthermore, the scattered light detector 52 is preferably disposed upstream of the light source 50.

Figure 13:
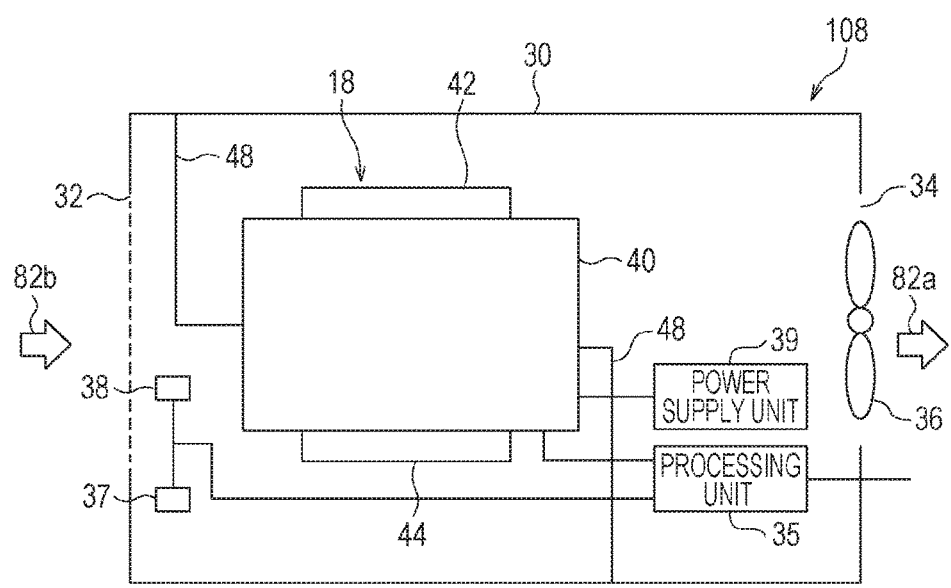
FIG. 13 schematically illustrates a measuring apparatus in a seventh modification of the second embodiment.

FIG. 13 schematically illustrates a measuring apparatus in a seventh modification of the second embodiment. In a measuring apparatus 108, the concentration measuring unit 18 lacks the exhaust fan 46 as illustrated in FIG. 13. Alternatively, the exhaust fan 46 is not operating. The inlet 42 and outlet 44 of the case 40 are separated from each other by the partition walls 48. The humidity sensor 38 and atmospheric pressure sensor 37 are disposed on the same side as the inlet 32 with respect to the partition walls 48. The power supply unit 39 and processing unit 35 are disposed on the same side as the outlet 34 with respect to the partition walls 48. In other respects, the structure is the same as in the second embodiment; their description will be omitted.

In the seventh modification of the second embodiment, only one exhaust fan, rather than two, is provided, so power consumption may be suppressed. Due to the partition walls 48, gas inhaled from the inlet 42 completely passes through the interior of the case 40 and is exhausted from the outlet 44. When the flow rate Q1 caused by the exhaust fan 36 is the same as the flow rate Q2 caused by the exhaust fan 46 in a case in which the concentration measuring unit 18 is used alone in the second embodiment (the concentration measuring unit 18 is not accommodated in the case 30), then the volume used in the measurement of particles 10 may be made the same as when the concentration measuring unit 18 is used alone. In the case in which the flow rates Q1 and Q2 differ from each other, when the measured particle number concentration is multiplied by Q1/Q2, the particle number concentration may be corrected. Furthermore, the particle number concentration may be corrected again in a state in which the concentration measuring unit 18 is accommodated in the case 30.

Third Embodiment

Figure 14:
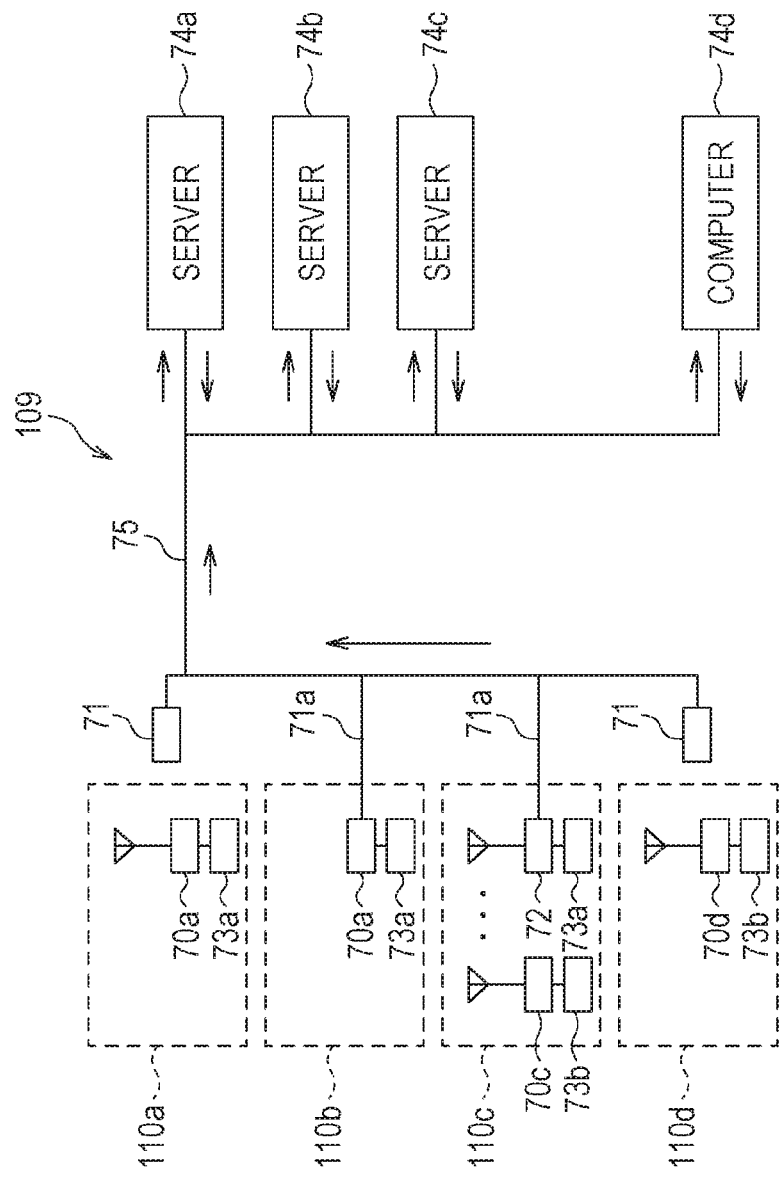
FIG. 14 is a block diagram of a measuring system in a third embodiment.

A third embodiment is an example of a PM2.5 measuring system in which the measuring apparatus in the first embodiment, the second embodiment, or its modification is used. FIG. 14 is a block diagram of a measuring system in the third embodiment. A measuring system 109 includes measuring apparatuses 70a to 70d, Internet service provider apparatus (ISP apparatus) 71, a relay apparatus 72, commercial power supplies 73a, a solar cell 73b, servers 74a to 74c, and a computer 74d. The measuring apparatuses 70a to 70d, ISP apparatus 71, relay apparatus 72, servers 74a to 74c, and computer 74d are mutually connected through an Internet network 75. The measuring apparatuses 70a to 70d are each any one of the measuring apparatus in the first embodiment, the second embodiment, and its modifications; they measure the particle number concentration of particles with diameters of about 2.5 µm or less. The measuring apparatuses 70a to 70d are respectively installed in installation places 110a to 110d. The data collection server 74a collects concentration information about particles 10 from the measuring apparatuses 70a to 70d in the installation places 110a to 110d in real time. The data storage server 74b stores the collected concentration information. The data delivery server 74c delivers the stored concentration information to the computer 74d.

The installation place 110a is, for example, an outdoor place of a business facility. It is assumed that in a place where the measuring apparatus 70a is installed, the commercial power supply 73a is available but a wired local area network (LAN) 71a is unavailable. Therefore, the commercial power supply 73a is used as the power supply of the measuring apparatus 70a. Data transmission and reception between the measuring apparatus 70a and the data collection server 74a is performed by using the ISP apparatus 71 through a wireless network such as a mobile communication network.

The installation place 110b is, for example, an indoor place of a personal house. It is assumed that in a place where the measuring apparatus 70b is installed, the commercial power supply 73a and wired LAN 71a are available. Therefore, the commercial power supply 73a is used as the power supply of the measuring apparatus 70b. Data transmission and reception between the measuring apparatus 70b and the data collection server 74a is performed through a wired LAN 71a.

The installation place 110c is, for example, an outdoor place of a school. It is assumed that in a place where the measuring apparatus 70c is installed, neither the commercial power supply 73a nor the wired LAN 71a is available. However, it is assumed that in an area including the installation place 110c there is a place where the commercial power supply 73a and wired LAN 71a are available. Therefore, the solar cell 73b is used as the power supply of the measuring apparatus 70c. The relay apparatus 72 is installed in the installation place 110c. The commercial power supply 73a is used as the power supply of the relay apparatus 72. In data transmission and reception between the measuring apparatus 70c and the relay apparatus 72, specified low power radio or other radio are used. In data transmission and reception between the relay apparatus 72 and the data collection server 74a, the wired LAN 71a is used. Data transmission and reception between the measuring apparatus 70c and the data collection server 74a is performed through the relay apparatus 72 and wired LAN 71a in this way.

The installation place 110d is in a mountain. It is assumed that in a place where the measuring apparatus 70d is installed, neither the commercial power supply 73a nor the wired LAN 71a is available. Further, it is assumed that in the installation place 110d, there is no place where the commercial power supply 73a or wired LAN 71a is available. Therefore, the solar cell 73b is used as the power supply of the measuring apparatus 70d. Data transmission and reception between the measuring apparatus 70d and the data collection server 74*a* is performed by using the ISP apparatus 71 through a wireless network such as a mobile communication network.

As described above, the commercial power supply 73*a*, solar cell 73*b*, or other various power supplies may be appropriately used as the power supplies of the measuring apparatuses 70*a* to 70*d*. In data transmission and reception between the measuring apparatuses 70*a* to 70*d* and the data collection server 74*a*, a wired LAN, a mobile communication network, a network using specified low-power radio, or networks in other various communication methods may be appropriately used.

In the measuring apparatuses 70*a* to 70*d*, a mass concentration may be calculated from the particle number concentration of particles 10. The measuring apparatuses 70*a* to 70*d* may send data about the particle number concentration of particles 10 and data about humidity to the data collection server 74*a*, and the data collection server 74*a* may calculate the mass concentration. A computer that calculates the mass concentration may be provided separately from the data collection server 74*a*.

Any value may be set as an interval at which the measuring apparatuses 70*a* to 70*d* send information of a PM2.5 concentration to the data collection server 74*a*. When a scattered light detection method is used at the measuring apparatuses 70*a* to 70*d*, it is also possible to send information of a PM2.5 concentration at intervals of, for example, one second. Information of PM2.5 concentrations may be collected in real time in this way.

The user uses a web browser of the computer 74*d* to access the data delivery server 74*c*. The data delivery server 74*c* may supply measured values of PM2.5 concentrations from PM2.5 concentration data stored in the data storage server 74*b*, in response to a request from the computer 74*d*. As the PM2.5 concentrations, values measured in real time or previously measured values of PM2.5 concentrations may be supplied.

Figure 15:
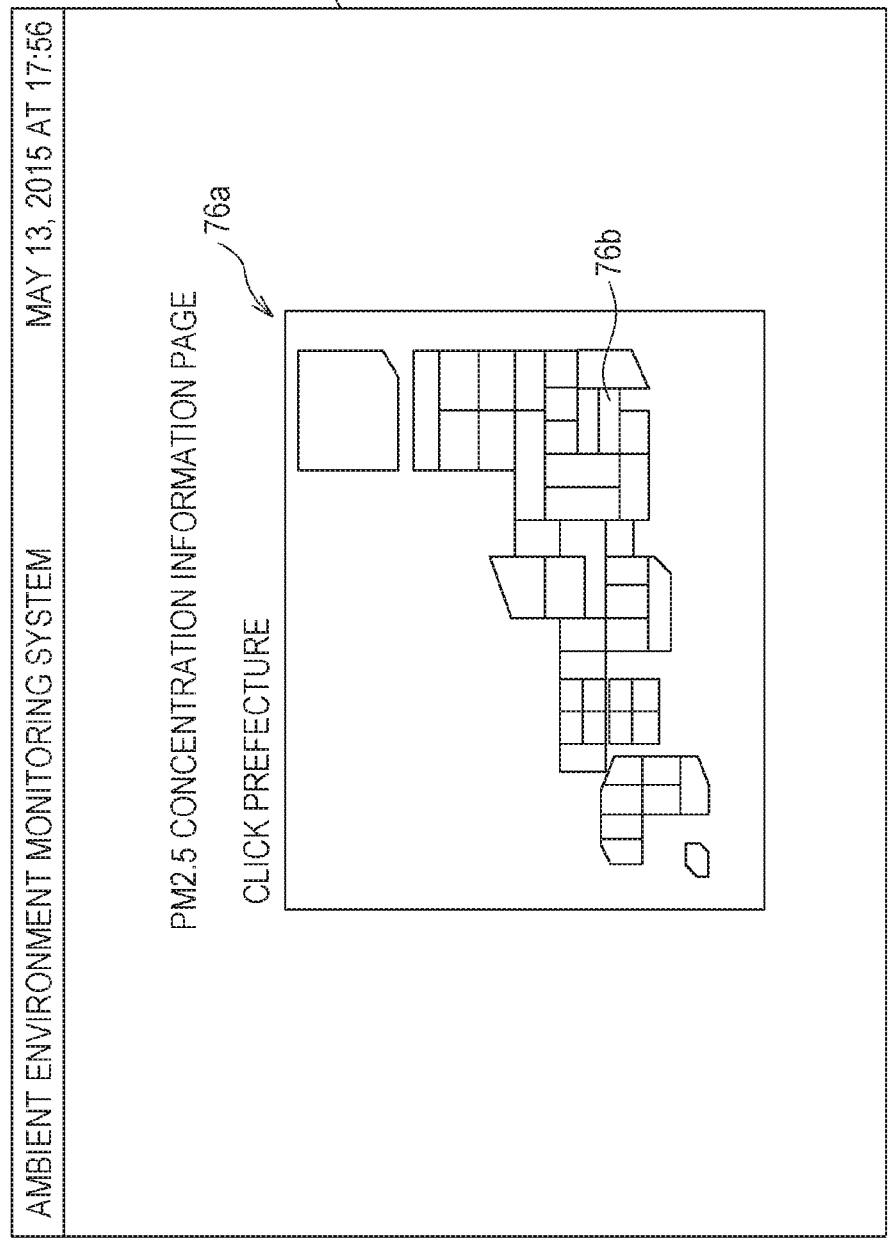
FIG. 15 illustrates an example of a computer screen.
Figure 16:
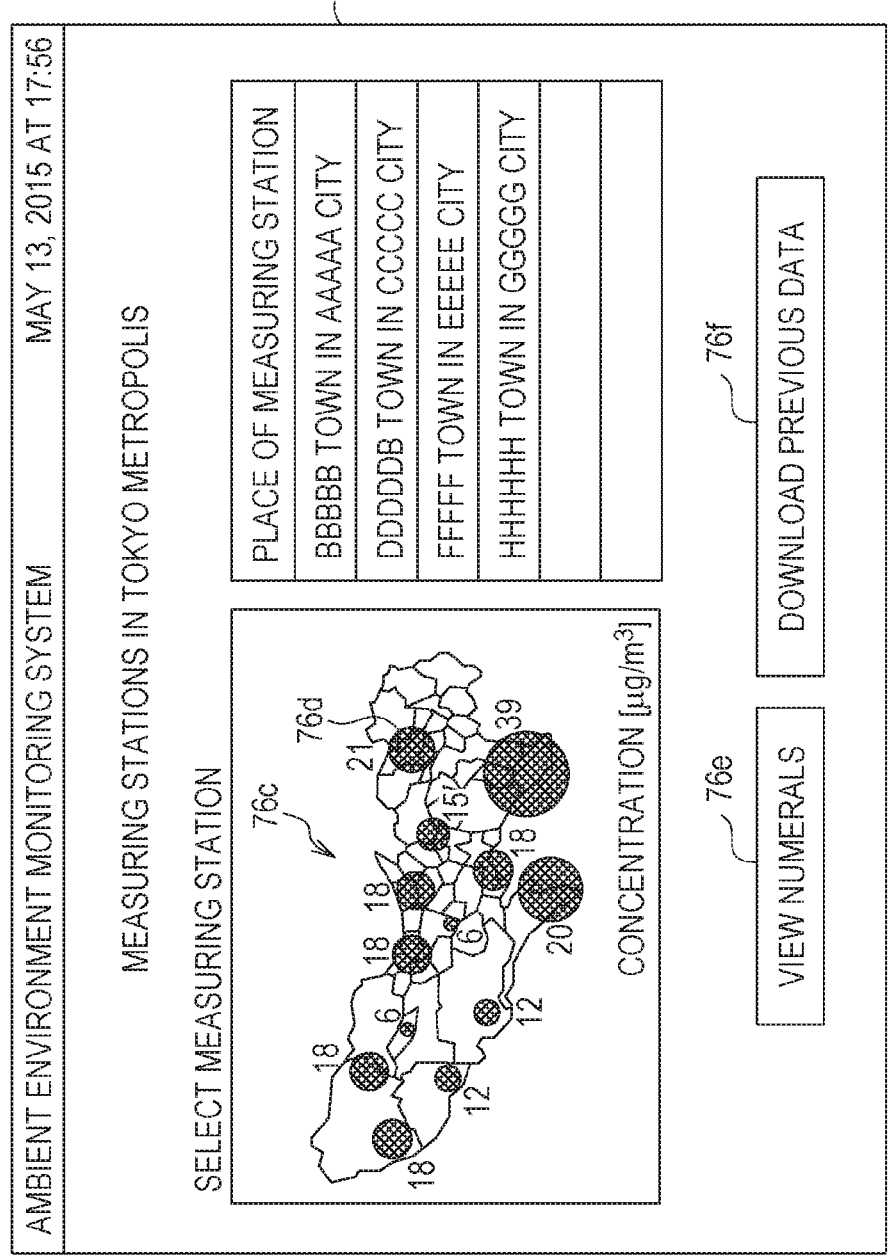
FIG. 16 illustrates an example of a computer screen.

FIGS. 15 to 17 illustrate examples of computer screens. When the data delivery server 74*c* is accessed, a Japanese map 76*a* is displayed as a PM2.5 concentration information page on a screen 78 of the computer 74*d*, as illustrated in FIG. 15. The message "Click prefecture" is displayed on the screen 78. A prefecture on the Japanese map 76*a* is clicked. For example, Tokyo Metropolis 76*b* is clicked.

As information about measuring stations in the Tokyo Metropolis, a map 76*c* of the Tokyo Metropolis and the places of the measuring stations are displayed on the screen 78 of the computer 74*d*, as illustrated in FIG. 16. The places of the measuring stations are the places where the measuring apparatuses 70*a* to 70*d* are installed. Circles 76*d*, each of which is centered at the place of a measuring station, are displayed on the map 76*c*. The size of each circle 76*d* is proportional to the PM2.5 concentration. A number indicated near the circle 76*d* is a PM2.5 concentration in $\mu g/m^3$. Since a PM2.5 concentration is represented as the size of the circle 76*d*, the user may visually recognize the PM2.5 concentrations and a distribution of PM2.5. A hierarchy of detailed maps may be further provided below the circle 76*d*. A banner 76*e* indicating "View numerals" and a banner 76*f* indicating "Download previous data" are displayed on the screen. When the banner 76*e* is clicked, the message "Select measuring station" is displayed on the map 76*c*. The station at which numerals are to be viewed is clicked.

As illustrated in FIG. 17, ambient environmental data in the BBBBB Town in the AAAAA City is displayed. The data is, for example, data measured in last 20 minutes. Temperature, humidity, atmospheric pressure, and PM2.5 concentrations at the measuring station are displayed in time series together with times of the day. When the banner 76*f* is clicked in FIG. 16 and a measuring station is clicked, previous time-series data may be downloaded in, for example, comma-separated values (CSV) format.

In the third embodiment, mass concentrations of particles may be obtained from the measuring apparatuses 70*a* to 70*d*, which are compact and inexpensive. Thus, a large number of measuring apparatuses 70*a* to 70*d* may be easily installed. When the measuring apparatuses 70*a* to 70*d* are connected to the servers 74*a* to 74*d* and computer 74*d* through the Internet network 75, the user may use the computer 74*d* to know a PM2.5 concentration in a desired region in real time. Since the intervals of measurements by the measuring apparatuses 70*a* to 70*d* may be set to, for example, 1 second, a trend of PM2.5 in the ambient air may be finely grasped.

Although, in the third embodiment, PM2.5 has been taken as an example, mass concentrations of particles other than PM2.5 may also be measured.

Embodiments of the present disclosure have been described in detail, but the present disclosure is not limited to particular embodiments. Various modifications and changes are possible without departing from the intended scope of the present disclosure described in the claims.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A measuring apparatus comprising:
   a concentration measuring unit including a concentration measuring instrument that measures a particle number concentration of a particle in gas;
   a humidity measuring unit that measures humidity of a surrounding to which the particle in gas is exposed when the concentration measuring unit measures the particle number concentration, the humidity measured by the humidity measuring unit being used to calculate a mass concentration of the particle in gas from information for indicating a correlation of a mass of the particle in gas to the humidity of the surrounding to which the particle in gas is exposed, the particle number concentration measured by the concentration measuring unit, and the humidity of the surrounding to which the particle in gas is exposed, the humidity measuring unit being a humidity sensor;
   a first case in which the concentration measuring unit and the humidity measuring unit are accommodated, the first case having a first inlet and a first outlet; and
   a first fan that exhausts the gas in the first case from the first outlet; wherein
   the humidity measuring unit is disposed upstream of the concentration measuring unit in a flow path of the gas from the first inlet to the first outlet, wherein:
   the concentration measuring unit has a second case with a second inlet and a second outlet and also has a second fan that exhausts the gas in the second case from the second outlet;

the flow path of the gas from the first inlet to the first outlet includes a flow path that passes through an interior of the second case and a flow path that passes between the first case and the second case without passing the interior of the second case; and a flow rate caused by the first fan is larger than a flow rate caused by the second fan.

2. The measuring apparatus according to claim 1, wherein when n designates an interval of measurements by the concentration measuring unit and V designates a volume of a space, in the flow path of the gas from the first inlet to the first outlet, between the first case and the second case from the second inlet to the first inlet, then the flow rate caused by the first fan is V/n or more.

3. The measuring apparatus according to claim 2, wherein the space is enclosed by the second case, an internal surface including the first inlet, the internal surface being part of the first case, and a plane that is orthogonal to a gas flow direction in the second case and includes an end of the second inlet in a downstream direction of gas flow in the second case.

4. The measuring apparatus according to claim 1, wherein:
the concentration measuring unit has a second case with a second inlet and a second outlet;
the concentration measuring unit lacks a second fan that exhausts the gas in the second case from the second outlet;
the flow path of the gas from the first inlet to the first outlet lacks a flow path that passes between the first case and the second case without passing an interior of the second case; and
the concentration measuring unit is disposed in a space between the first case and the second case from the second inlet to the first inlet.

5. The measuring apparatus according to claim 1, wherein the concentration measuring unit uses a scattered light detection method to measure the particle number concentration.

6. The measuring apparatus according to claim 1, further comprising a calculating unit that calculates the mass concentration of the particle in gas from the information indicating the correlation of the mass of the particle in gas to the humidity of the surrounding to which the particle in gas is exposed, the particle number concentration measured by the concentration measuring unit, and the humidity of the surrounding to which the particle in gas is exposed, the calculating unit being a computer or a processor.

7. The measuring apparatus according to claim 1, wherein when a direction in which the second inlet and the second outlet are placed is parallel to a direction of gas flow in the first case, the humidity measuring unit is disposed in a space enclosed by the second case, an internal surface including the first inlet, the internal surface being part of the first case, and a plane that is orthogonal to a gas flow direction in the second case and includes an end of the second inlet in a downstream direction of gas flow in the second case.

8. The measuring apparatus according to claim 1, wherein when a direction in which the second inlet and the second outlet are placed differs from a direction of gas flow in the first case, the humidity measuring unit is disposed in a space enclosed by the second case, an internal surface including the first inlet, the internal surface being part of the first case, a plane that is orthogonal to a gas flow direction in the second case and includes an end of the second inlet in a downstream direction of gas flow in the second case, and a plane that passes a midpoint between a center of the second inlet and a center of the second outlet and is orthogonal to a straight line for connecting the center of the second inlet and the center of the second outlet.

9. The measuring apparatus according to claim 1, further comprising an atmospheric pressure sensor that measures atmospheric pressure used to correct the particle number concentration measured by the concentration measuring unit, wherein
the atmospheric pressure sensor is disposed upstream of the concentration measuring unit in the flow path of the gas from the first inlet to the first outlet.

10. The measuring apparatus according to claim 1, wherein: the humidity measuring unit is disposed upstream of the entire concentration measuring instrument disposed in the flow path of the gas from the first inlet to the first outlet.

11. A measuring apparatus comprising:
a concentration measuring unit including a concentration measuring instrument that measures a particle number concentration of a particle in gas;
a humidity measuring unit that measures humidity of a surrounding to which the particle in gas is exposed when the concentration measuring unit measures the particle number concentration, the humidity measured by the humidity measuring unit being used to calculate mass concentration of the particle in gas from information for indicating a correlation of a mass of the particle in gas to the humidity of the surrounding to which the particle in gas is exposed the particle number concentration measured by the concentration measuring unit, and the humidity of the surrounding to which the particle in gas is exposed, the humidity measuring unit being a humidity sensor;
a first case in which the concentration measuring unit and the humidity measuring unit are accommodated, the first case having a first inlet and a first outlet;
a first fan that exhausts the gas in the first case from the first outlet; wherein
the humidity measuring unit is disposed upstream of the concentration measuring unit in a flow path of the gas from the first inlet to the first outlet; and
a power supply that supplies electric power to the concentration measuring unit, wherein
the power supply is disposed downstream of the concentration measuring unit in the flow path of the gas from the first inlet to the first outlet.

12. A measuring system comprising a measuring apparatus that includes:
a concentration measuring unit, including a concentration measuring instrument, that measures a particle number concentration of a particle in gas,
a humidity measuring unit that measures humidity of a surrounding to which the particle in gas is exposed when the concentration measuring unit measures the particle number concentration,
a first case in which the concentration measuring unit and the humidity measuring unit are accommodated, the first case having a first inlet and a first outlet, the humidity measuring unit being disposed upstream of the concentration measuring unit in a flow path of the gas from the first inlet to the first outlet, and
a first fan that exhausts the gas in the first case from the first outlet; and
a calculating unit that calculates a mass concentration of the particle in gas from information for indicating a correlation of a mass of the particle in gas to the humidity of the surrounding to which the particle in gas is exposed, the particle number concentration measured by the concentration measuring unit, and the humidity of the surrounding to which the particle in gas is exposed, the calculating unit being a computer or a processor, wherein:

the concentration measuring unit has a second case with a second inlet and a second outlet and also has a second fan that exhausts the gas in the second case from the second outlet;

the flow path of the gas from the first inlet to the first outlet includes a flow path that passes through an interior of the second case and a flow path that passes between the first case and the second case without passing the interior of the second case; and a flow rate caused by the first fan is larger than a flow rate caused by the second fan.

13. The measuring system according to claim 12, wherein: the humidity measuring unit is disposed upstream of the entire concentration measuring instrument disposed in the flow path of the gas from the first inlet to the first outlet.

* * * * *